(12) United States Patent
Dugan et al.

(10) Patent No.: US 7,993,583 B2
(45) Date of Patent: Aug. 9, 2011

(54) PASSIVE MICROFLUIDIC ARRAY CARD AND READER

(75) Inventors: Lawrence Christopher Dugan, Modesto, CA (US); Matthew A. Coleman, Oakland, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 156 days.

(21) Appl. No.: 12/574,095

(22) Filed: Oct. 6, 2009

(65) Prior Publication Data

US 2010/0105577 A1   Apr. 29, 2010

Related U.S. Application Data

(60) Provisional application No. 61/109,234, filed on Oct. 29, 2008.

(51) Int. Cl.
| | | |
|---|---|---|
| *G01N 21/00* | (2006.01) | |
| *G01N 33/543* | (2006.01) | |
| *C12M 3/00* | (2006.01) | |
| *G01N 33/53* | (2006.01) | |
| *C40B 60/12* | (2006.01) | |

(52) U.S. Cl. ............ 422/64; 422/63; 422/65; 422/68.1; 422/82.05; 435/6; 435/7.1; 435/287.2; 435/287.3; 435/288.7; 436/164; 436/518; 436/527; 506/39

(58) Field of Classification Search .................. None
See application file for complete search history.

(56) References Cited

U.S. PATENT DOCUMENTS

| | | | |
|---|---|---|---|
| 6,818,435 | B2 | 11/2004 | Carvalho et al. |
| 7,033,747 | B2 | 4/2006 | Gordon |
| 7,141,416 | B2 | 11/2006 | Krutzik |
| 2003/0003464 | A1 | 1/2003 | Phan et al. |
| 2008/0166793 | A1 | 7/2008 | Beer et al. |

FOREIGN PATENT DOCUMENTS

GB   2 341 924 A   3/2000

OTHER PUBLICATIONS

N. Reginald Beer, On-Chip Single-Copy Real-Time Reverse-Transcription PCR in Isolated Picoliter Droplets, Analytical Chemistry, vol. 80, No. 6, Mar. 15, 2008 pp. 1854-1858.

*Primary Examiner* — Jill Warden
*Assistant Examiner* — Neil Turk
(74) *Attorney, Agent, or Firm* — Eddie E. Scott; James S. Tak (57) ABSTRACT

A microfluidic array card and reader system for analyzing a sample. The microfluidic array card includes a sample loading section for loading the sample onto the microfluidic array card, a multiplicity of array windows, and a transport section or sections for transporting the sample from the sample loading section to the array windows. The microfluidic array card reader includes a housing, a receiving section for receiving the microfluidic array card, a viewing section, and a light source that directs light to the array window of the microfluidic array card and to the viewing section.

19 Claims, 7 Drawing Sheets

PASSIVE MICROFLUIDIC ARRAY CARD AND READER

CROSS-REFERENCE TO RELATED APPLICATIONS

The present application claims benefit under 35 U.S.C. §119(e) of U.S. Provisional Patent Application No. 61/109,234 filed Oct. 29, 2008 entitled "Passive Microfluidic Array Card and Reader," the disclosure of which is hereby incorporated by reference in its entirety for all purposes.

STATEMENT AS TO RIGHTS TO INVENTIONS MADE UNDER FEDERALLY SPONSORED RESEARCH AND DEVELOPMENT

The United States Government has rights in this invention pursuant to Contract No. DE-AC52-07NA27344 between the United States Department of Energy and Lawrence Livermore National Security, LLC for the operation of Lawrence Livermore National Laboratory.

BACKGROUND

1. Field of Endeavor

The present invention relates to sample analysis and more particularly to a microfluidic array card and reader for analyzing a sample.

2. State of Technology

U.S. Pat. No. 6,818,435 to Bruce L. Cavalho et al for microfluidics devices and methods for performing cell based assays provides the state of technology information set out below. The disclosure of U.S. Pat. No. 6,818,435 is incorporated herein in its entirety by this reference.

Recent developments in a variety of investigational and research fields have created a need for improved methods and apparatus for performing analytical, particularly bioanalytical assays at microscale (i.e., in volumes of less than 100 µL). In the field of pharmaceuticals, an increasing number of potential drug candidates require assessment of their biological function. As an example, the field of combinatorial chemistry combines various structural sub-units with differing chemical affinities or configurations into molecules; in theory, a new molecule having potentially unique biochemical properties can be created for each permutation of the sub-units. In this way, large libraries of compounds may be synthesized from relatively small numbers of constituents, each such compound being a potential drug lead compound of usually unknown biological activity and potency. Similarly, increasingly large numbers of targets for these putative therapeutic compounds are being discovered, many as a result of the growing information derived from such large-scale biological research as the sequencing of the human genome.

U.S. Pat. No. 7,033,747 to John Francis Gordon for multi-parameter assays including analysis discs and methods relating thereto provides the state of technology information set out below. The disclosure of U.S. Pat. No. 7,033,747 is incorporated herein in its entirety by this reference.

There is a significant need to make diagnostic assays and forensic assays of all types faster and more local to the end-user. Ideally, clinicians, patients, investigators, the military, other health care personnel, and consumers should be able to test themselves for the presence of certain factors or indicators in their systems, and for the presence of certain biological material at a crime scene or on a battlefield. At present, there are a number of silicon-based chips with nucleic acids and/or proteins attached thereto, which are commercially available or under development, for performing biomedical, chemical, or biochemical assays. These chips are not for use by the end-user, or for use by persons or entities lacking very specialized expertise and expensive equipment. It is an object of the present invention to obviate or mitigate at least one of these disadvantages by use of a relatively inexpensive assay system that can be used by the end user without specialized training.

U.S. Pat. No. 7,141,416 to Siegfried Richard Krutzik for multi-purpose optical analysis optical bio-disc for conducting assays and various reporting agents for use therewith provides the state of technology information set out below. The disclosure of U.S. Pat. No. 7,141,416 is incorporated herein in its entirety by this reference.

The detection and quantification of analytes in the blood or other body fluids are essential for diagnosis of diseases, elucidation of the pathogenesis, and for monitoring the response to drug treatment. Traditionally, diagnostic assays are performed in laboratories by trained technicians using complex apparatus. Performing these assays is usually time-consuming and costly. Thus, there is a significant need to make diagnostic assays and forensic assays of all types faster and more local to the end-user. Ideally, clinicians, patients, investigators, the military, other health care personnel, and consumers should be able to test themselves for the presence of certain risk factors or disease indicators in their systems, and to test for the presence of certain biological material at a crime scene or on a battlefield. At present, there are a number of medical diagnostic, silicon-based, devices with nucleic acids and/or proteins attached thereto that are commercially available or under development. These chips are not for use by the end-user, or for use by persons or entities lacking very specialized expertise and expensive equipment.

United States Published Patent Application No. 2003/0003464 by Brigitte C. Phan for dual bead assays including optical biodiscs and methods relating thereto provides the state of technology information set out below. The disclosure of United States Published Patent Application No. 2003/0003464 is incorporated herein in its entirety by this reference.

There is a significant need to make diagnostic assays and forensic assays of all types faster and more local to the end-user. Ideally, clinicians, patients, investigators, the military, other health care personnel and consumers should be able to test themselves for the presence of certain factors or indicators in their systems, for the presence of certain biological material at a crime scene or on a battlefield. At present, there are a number of silicon based chips with nucleic acids and/or proteins attached thereto which are commercially available or under development. These chips are not for use by the end-user, or for use by persons or entities lacking very specialized expertise and expensive equipment.

UK Patent Application No. GB 2,341,924 A for a microfluidic device provides the state of technology information set out below. The disclosure of UK Patent Application No. GB 2,341,924 A is incorporated herein in its entirety by this reference.

It has now been found that microfluidic devices can be prepared in which fluid flow may be controlled by having different surfaces of the substrate forming the device having different surface characteristics. By "microfluidic devices" is meant devices that can handle microvolumes of reagents, for example samples of less than 9 μl, suitably less than 500 nl and preferably between 1 and 10 nl, may be introduced into the device. By "fluid" is meant dry powders and liquids, including suspensions of particulates in liquids.

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention provides a microfluidic array card and reader system for analyzing a sample. In one embodiment the microfluidic array card and reader system includes a microfluidic array card. The microfluidic array card includes a sample loading section for loading the sample onto the microfluidic array card. The microfluidic array card includes a multiplicity of array windows and a transport section or sections for transporting the sample from the sample loading section to the array windows. The microfluidic array card reader includes a housing, a receiving section for receiving the microfluidic array card, a viewing section, and a light source that directs light to the array window of the microfluidic array card and to the viewing section.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF SPECIFIC EMBODIMENTS

Referring to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

Figure 1:
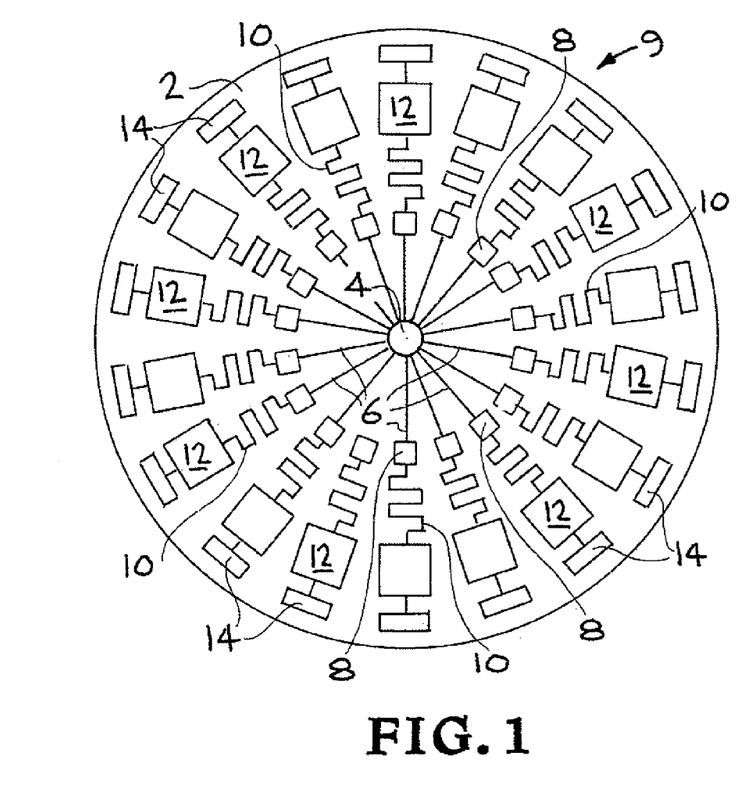
FIG. 1 illustrates a disposable microfluidic array card.

Referring now to the drawings and in particular to FIG. 1, one embodiment of a system of the present invention is illustrated. The present invention provides a microfluidic array card and reader for analyzing a sample. The microfluidic array card is inserted into the reader and each array is viewed for positive signatures. Uses of this invention include identifying biological threat agents; identifying biological signatures of exposures to pathogens, radiation, toxins, or chemicals, identifying markers of disease; and identification of other substances.

FIG. 1 illustrates a disposable microfluidic array card 9. This disposable microfluidic array card 9 utilizes passive capillary action to flow a sample solution from a sample loading position to multiple assay array positions located at uniform distances around the outer diameter of a circular card. The arrays may consist of a minimum number of spots ranging in diameter from 1 to 350 micrometers in size. These spots may be made up of synthetic nucleic acids conjugated to the surface, to beads, or similar entities, antibodies conjugated to the surface, or beads, or similar entities, or other capture technologies. The sample is uniformly distributed to each array by capillary action. Excess liquid is removed from the array by an absorbent material located after the array. Resulting assay signatures are obtained using a hand-held imaging device reader.

A series of windows is located around the perimeter of the card 9. A sample loading port is located centrally and connected to each array window with identical flow channels. Alternatively, each array window can be connected to its own sample loading port. An absorbent fiber-based material is located near the window, on the opposite side of the sample loading port. Fluid from the sample port wicks across the array window, allowing analyte to bind to capture materials located in the array. Excess fluid is collected by the absorbent fiber. Sensitivity is increased by spotting small volumes of capture molecules in the array area.

Referring again to FIG. 1, the disposable microfluidic array card 9 is made with at least 2 layers. The first layer contains the chambers and capillary channels that will be described subsequently. The first layer is joined to a cover plate. The array card 9 includes the following components: Card Body 2, Lock Fitting 4, Capillary Pathways 6, Mixing Chambers 8, Serpentine Capillary Pathways 10, Detection Chambers (windows) 12, and Wicking Pads 14. The card body 2 includes a central port (i.e. a sample loading section) with a lock fitting. The central port is connected to capillary pathways 6 which in turn connect to mixing chambers 8. From mixing chambers 8 serpentine capillary pathways 10 lead to the detection chambers 12. Capillaries 6, mixing chambers 8, and serpentine capillary pathways 10 provide a transport section or sections for transporting the sample from the sample loading section to the windows 12.

The array card 9 is visualized through a view finder reader that utilizes ambient light to provide contrast to gold, silver, nickel, or other nanoparticles conjugated to the capture molecules or sample molecules. Alternatively, the view finder reader can be equipped with a simple light source such as a halogen bulb or light emitting diode and digital camera chip. The view finder can be connected to a computer via a USB port for capturing, recording, and analyzing the arrays.

Figure 2:
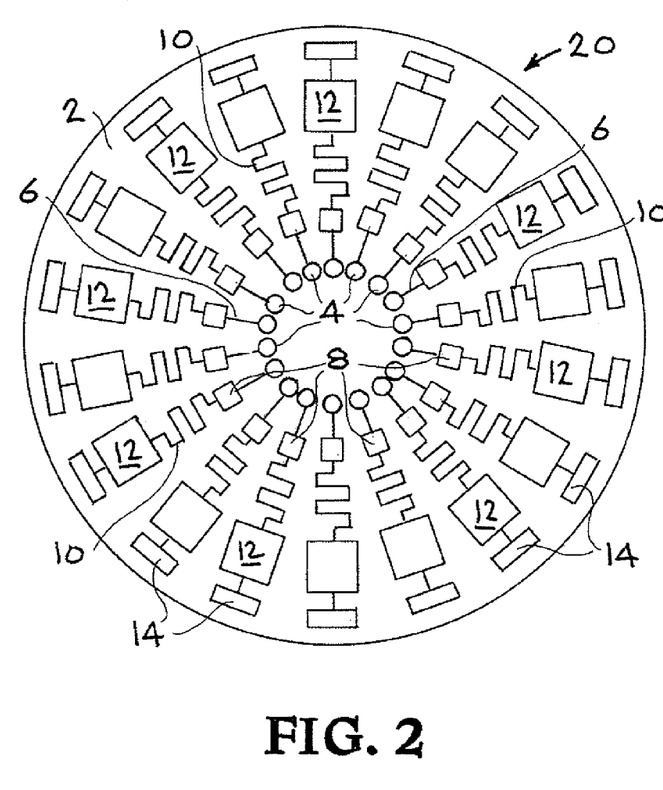
FIG. 2 illustrates another disposable microfluidic array card.

FIG. 2 illustrates a disposable microfluidic array card 20 that is similar to the card shown in FIG. 1. The difference between the FIG. 1 microfluidic array card 9 and microfluidic array card 20 is that instead of a single control port for receiving samples, each detection site 12 will have a separate entry port 4 with the lock fitting. This card 20 is also shown with 18 detection sites 12 but can be manufactured with more or less sites. The microfluidic array card 20 includes the following components Card Body 2, Lock Fitting 4, Capillary pathways 6, Mixing chambers 8, Serpentine capillary pathways 10, Detection chamber 12, and Wicking pad 12.

Figure 3:
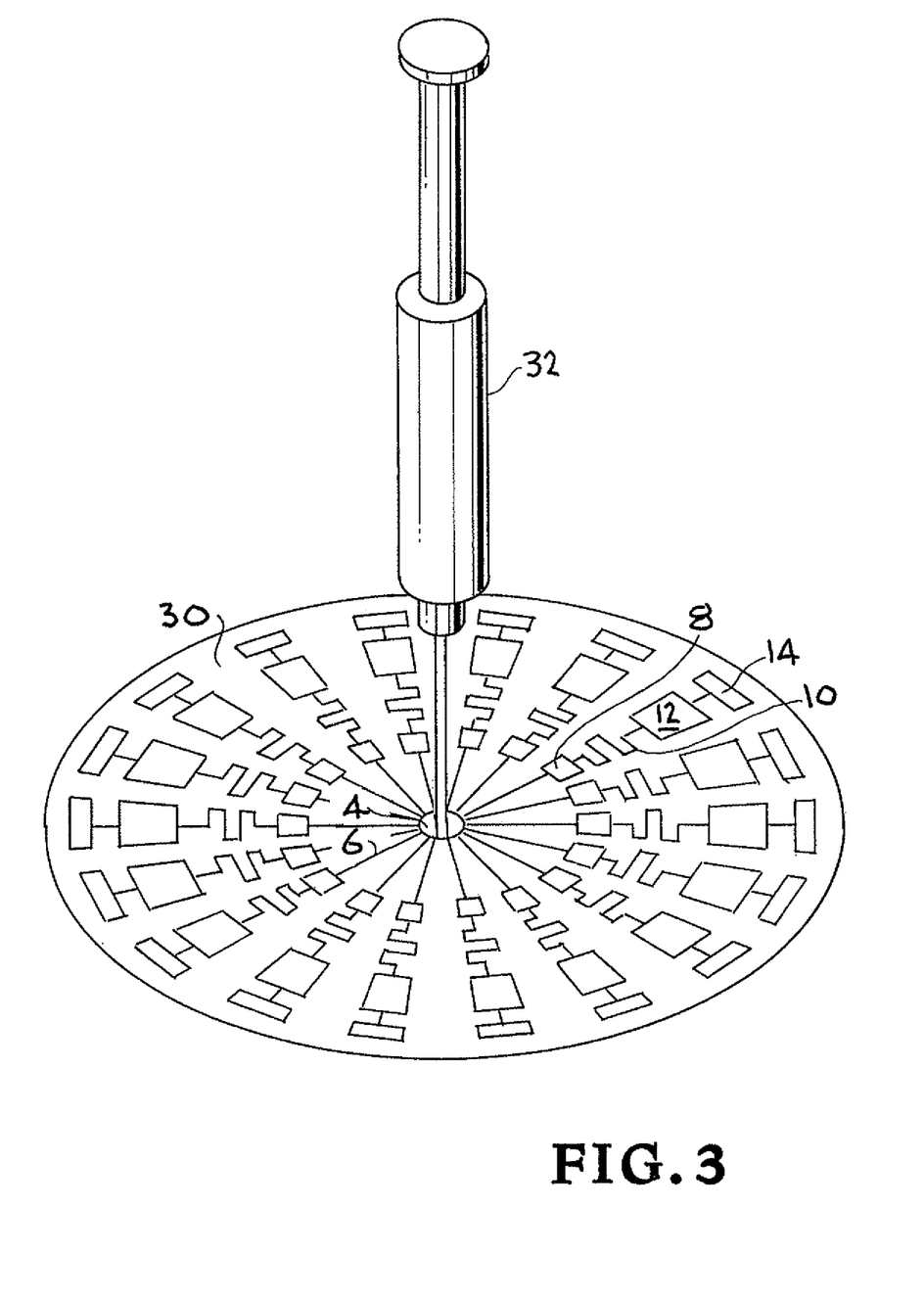
FIG. 3 illustrates a method of loading a sample into a disposable microfluidic array card.

FIG. 3 illustrates a method of loading a sample into a disposable microfluidic array card 30. A syringe 32 is loaded with a sample. The syringe 32 is equipped with a male lock fitting. The male fitting on the syringe connects to a female lock fitting on the port 4 of the card 30. Pressure produced during plunging of the syringe 32 forces the sample suspension into the capillary pathways towards the assay array positions on the card 30 capillary action maintains flow of the sample. A wicking pad 14 may be located past the array positions to assist in flow of the sample.

Samples mix and bind with detection molecules in chamber 8 and continue along the inscribed flow path 10 toward the detection chamber window 12. The sample mixed and bound with detection molecules enter the detection chamber window 12 and are localized by trap molecules bound in designated locations within the detection chamber 12. Utilization of specific nucleic acids, antibodies, or other capture technologies on the microfluidic array card allows for the detection of pathogenic and non-pathogenic microorganisms.

Bacteria detectable with the microfluidic array card and reader include Gram positive and Gram negative organisms of human, plant, animal, and environmental origin for which capture and detection molecules exist or could be readily prepared including, but not limited to; *Bacillus anthracis, Staphylococcus aureus, Pseudomonas aeruginosa, Streptococcus pneumonia, Escherichia coli, Francisella tularensis*, and *Yersinia pestis*.

Viruses detectable with the microfluidic array card and reader include RNA and DNA viruses of human, plant, or animal origin for which capture and detection molecules exist or could be readily prepared including, but not limited to; influenza virus, human immunodeficiency virus, rotoviruses, noroviruses, hepatitis, foot and mouth disease virus, blue tongue virus, and bovine viral diarrhea virus. Additional microorganisms for which capture and detection molecules exist or could be readily prepared and therefore detectable with the microfluidic array card and reader include yeast and fungi. Utilization of specific nucleic acids, antibodies, aptamers, or other capture technologies on the microfluidic array card allows for detection of biomarkers for exposure to ionizing radiation, infectious disease, cancer, heart disease, and other illness.

Figure 4:
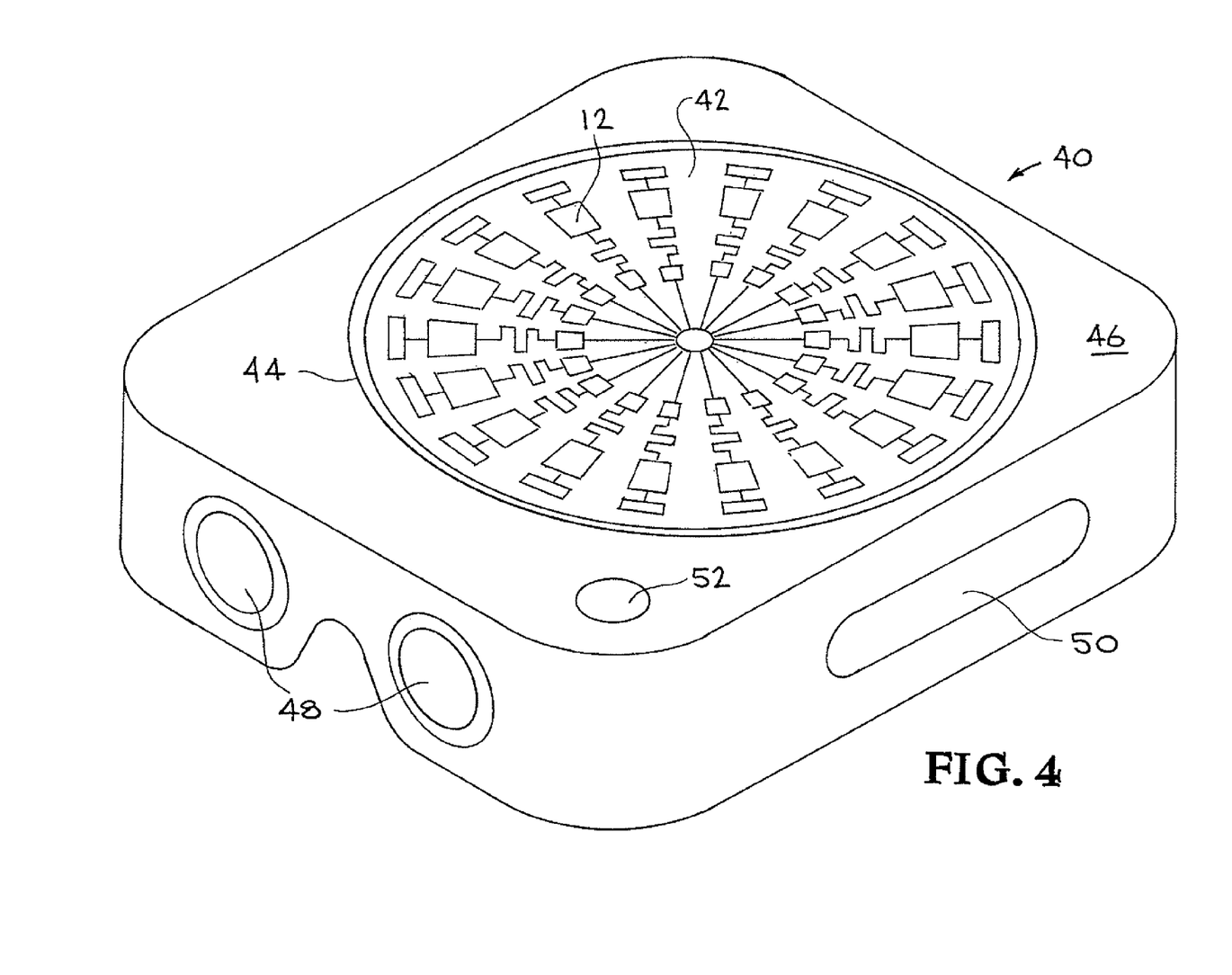
FIG. 4 illustrates one method of viewing data in the detection chambers of the disposable microfluidic array card.

FIG. 4 shows one method of viewing the data in the detection chambers (windows) 12 of the disposable microfluidic array card 42. The card 42 is placed in a receptacle 44 in the body 46 of the card reader 40. The card reader 40 has positions 50 for the hands of the person using the card reader. The user then can bring the card reader 40 to a position where the user can view the detection site or sites thru the eyepieces 48. The detection sites 12 can be illuminated either by available ambient light or by a light source internal to the card reader 40. The user can rotate the card to different positions to view other detection sites 12 on the card 42 by depressing button 52. The card reader 40 includes a light weight housing 46 with hand gripping sections 50 for enabling the person using the microfluidic array card and reader to view the detection sites 12 through the eyepieces 48.

Figure 5:
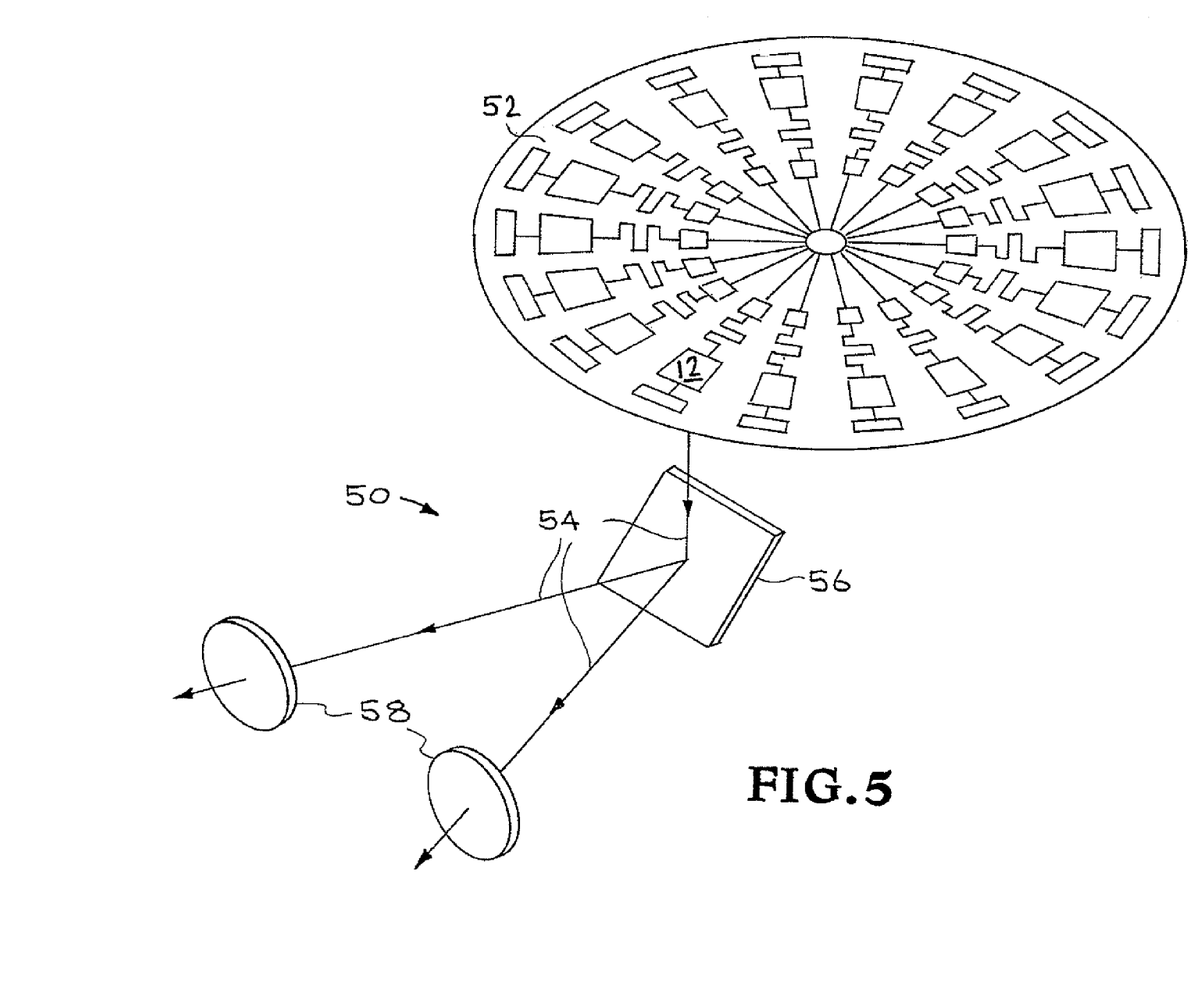
FIG. 5 illustrates a simple optical system viewing a detection site on a deposable microfluidic array card.

FIG. 5 shows a simple optical system 50 viewing a detection site 12 on a disposable microfluidic array card 52. The light path 54 with the image from the site 12 on card 52 is reflected by mirror 56 to the eye pieces 58 for viewing by the user.

Microfluidic Array Card and Reader Example

An example of a microfluidic array card and reader system for analyzing a sample of the present invention includes the following elements. A microfluidic array card is provided that includes a sample loading section for loading the sample onto the microfluidic array card and a multiplicity of array windows. A transport section or sections transports the sample from the sample loading section to the array windows. The microfluidic array card reader includes a housing, a receiving section for receiving the microfluidic array card, a viewing section, and a light source that directs light to the array window of the microfluidic array card and to the viewing section.

Protocol for Microfluidic Array Card and Reader

A syringe equipped with a male Luer-lock fitting and loaded with sample is connected to the female Luer-lock fitting located at the center of the disposable microfluidic array card. Samples, including bacteria, virus, yeast, or fungi suspensions, and purified proteins and protein complexes from saliva, oral swabs, nasal swabs, blood, including human and animal, or plant sources are then loaded onto the microfluidic array card by depressing the syringe plunger.

Pressure produced during plunging of the syringe forces the sample suspension into the capillary pathways towards the assay array positions. Capillary action maintains flow of the sample. A wicking pad may be located past the assay array positions to assist in flow of sample.

Samples mix and bind with detection molecules and continue along the inscribed flow path toward the detection chamber.

Sample/detection molecules enter detection chamber and are localized by trap molecules bound in designated locations within the detection chamber.

Visualization of the samples is performed via gold, silver, fluorescently-labeled, colored, or otherwise identifiable nanoparticles/reagents bound to the detection molecules.

Utilization of specific nucleic acids, antibodies, or other capture technologies on the Microfluidic Array Card allows for the detection of pathogenic and non-pathogenic microorganisms.

Bacteria detectable with the Microfluidic Array Card include Gram positive and Gram negative organisms of human, plant, animal, and environmental origin for which capture and detection molecules exist or could be readily prepared including, but not limited to; *Bacillus anthracis, Staphylococcus aureus, Pseudomonas aeruginosa, Streptococcus pneumoniae, Escherichia coli, Francisella tularensis*, and *Yersinia pestis*.

Viruses detectable with the Microfluidic Array Card include RNA and DNA viruses of human, plant, or animal origin for which capture and detection molecules exist or could be readily prepared including, but not limited to; influenza virus, human immunodeficiency virus, rotoviruses, noroviruses, hepatitis, foot and mouth disease virus, blue tongue virus, and bovine viral diarrhea virus.

Additional microorganisms for which capture and detection molecules exist or could be readily prepared and therefore detectable with the Microfluidic Array Card include yeast and fungi.

Utilization of specific nucleic acids, antibodies, aptamers, or other capture technologies on the Microfluidic Array Card allows for detection of biomarkers for exposure to ionizing radiation, infectious disease, cancer, heart disease, and other illness.

Figure 6:
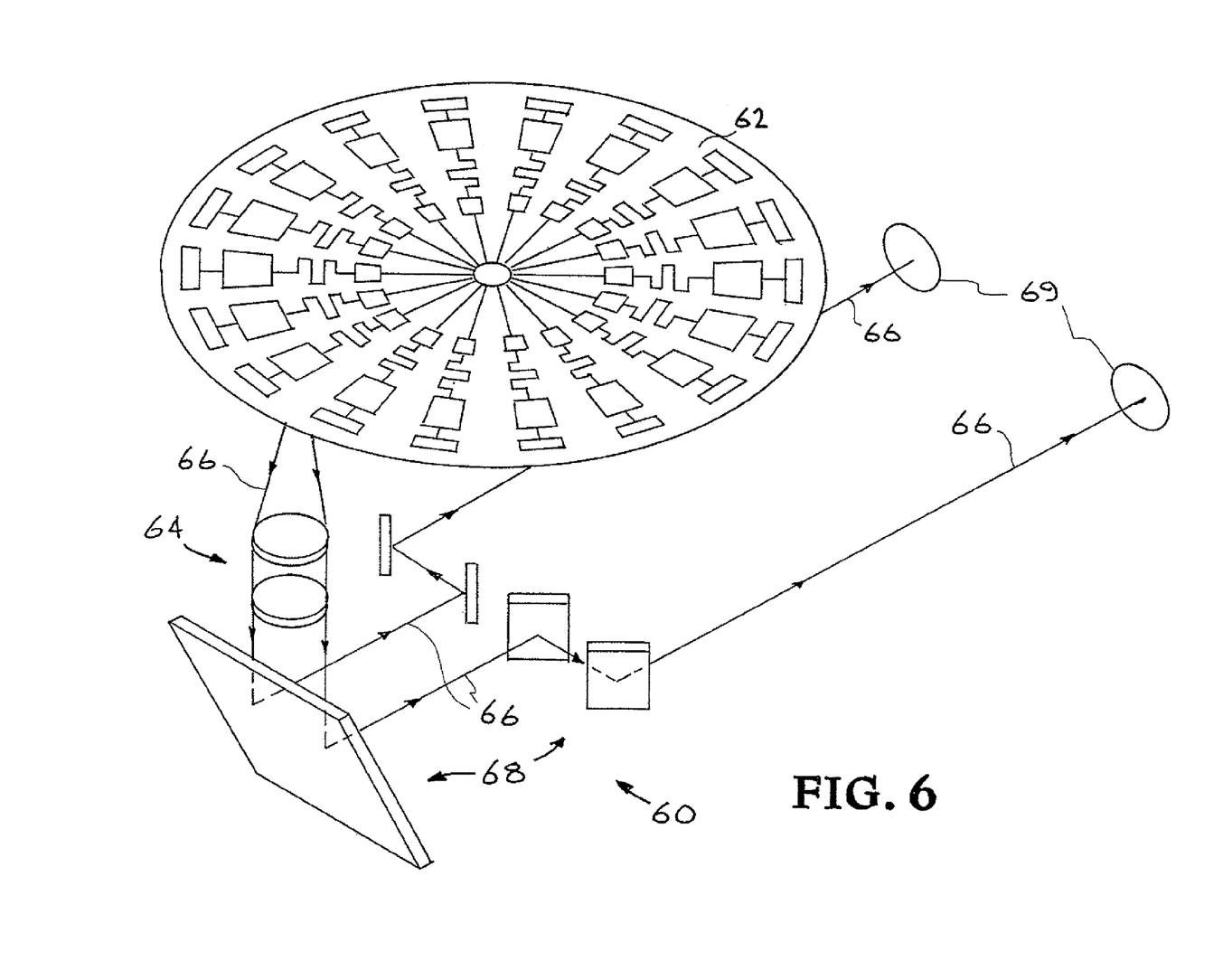
FIG. 6 illustrates a more complex optical system viewing a detection site on a deposable microfluidic array card.

FIG. 6 shows a more elaborate optical system 60. The image from detected site 12 on card 62 passes thru a system of lenses 64 than can either enlarge or reduce the image size. The light or image path then travels thru a system of mirrors 68 to the eyepieces 69 for viewing by the user. A light source directs light to the array window of the microfluidic array card and to the viewing section. The light source can be ambient light, a light bulb, a laser, or other light source. Systems for analyzing a sample utilizing a light source and array windows with a transport section for transporting the sample from the array windows are described in United States Published Patent Application No. 2008/0166793 by Neil R. Beer et al and the article, "On-Chip Single-Copy Real-Time Reverse-Transcription PCR in Isolated Picoliter proplets," by Reginald Beer, Elizabeth K. Wheeler, Lorenna Lee-Houghton, Nicholas Watkins, Shanavaz Nasarabadi, Nicole Hebert, Patrick Leung, Don W. Arnold, Christopher G. Bailey, and Bill W. Colston in Anal. Chem. 2008, 80, 1854-1858. United States Published Patent Application No. 2008/0166793 by Neil R. Beer et al and the article, "On-Chip Single-Copy Real-Time Reverse-Transcription PCR in Isolated Picoliter proplets," by Reginald Beer, Elizabeth K. Wheeler, Lorenna Lee-Houghton, Nicholas Watkins, Shanavaz Nasarabadi, Nicole Hebert, Patrick Leung, Don W. Arnold, Christopher G. Bailey, and Bill W. Colston in Anal. Chem. 2008, 80, 1854-1858 are incorporated herein by this reference.

Figure 7:
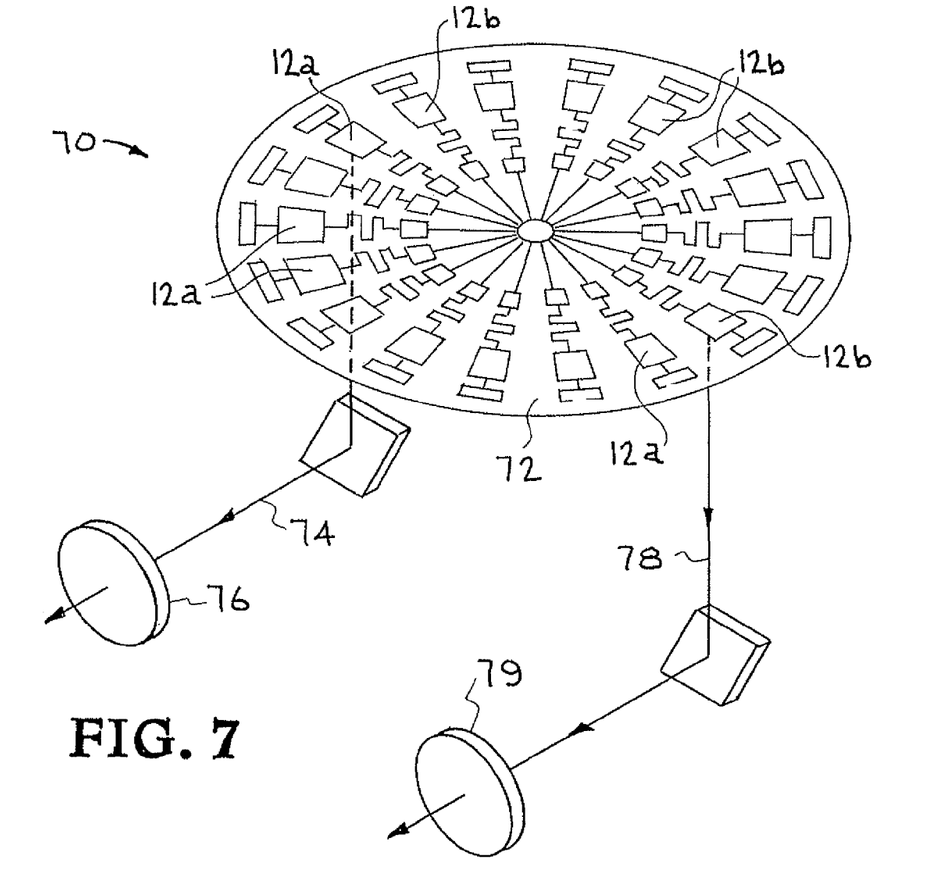
FIG. 7 depicts an optical system with two separate image paths.

FIG. 7 depicts an optical system 70 with 2 separate image paths. The sites labeled 12a receive samples introduced into the detection system. The image in the site 12a travels along the path 74 to eyepiece 76. The sites labeled 12b contain images that are used for comparison with the images from detection sites 12a. By comparing the two images the user can analyze the data presented from the detection sites 12a. The images in the sites labeled 12b are obtained from a library of known images. The known images in sites 12b can be changed to allow comparison of various know images with the sample image in sites 12a.

Figure 8:
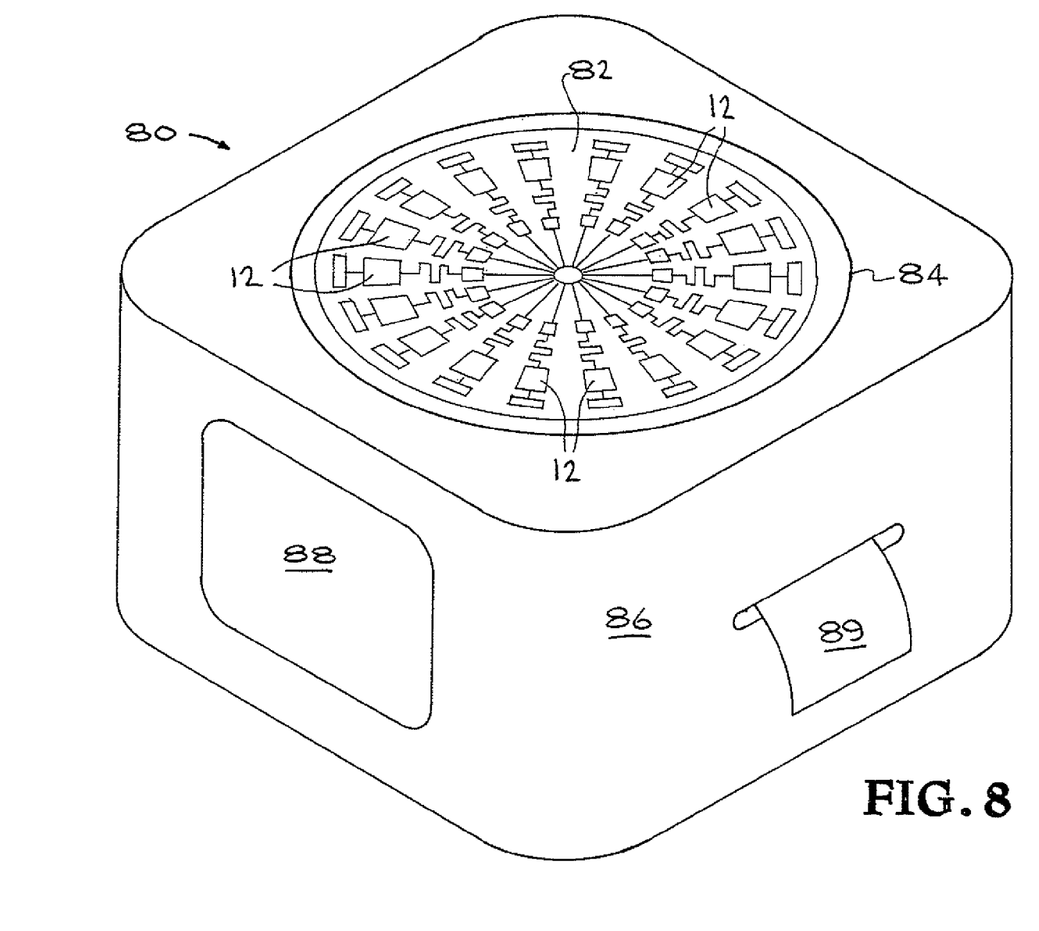
FIG. 8 illustrates a self contained system for analyzing data from a disposable microfluidic array card.

FIG. 8 is an illustration of a self contained system 80 for analyzing data from a disposable microfluidic array card 82. The card 82 is placed in a receptacle 84 on the body of apparatus 86. Apparatus has a means for analyzing the data contained in detection sites 12. The information can then be displayed on a view screen 88. A paper printout 89 can also be dispensed by apparatus 86.

Figure 9:
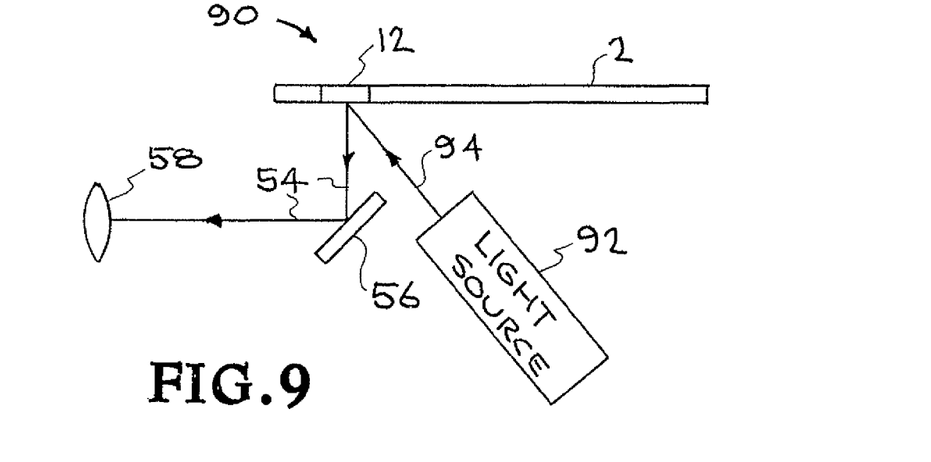
FIG. 9 illustrates another embodiment of an optical system viewing a detection site on a deposable microfluidic array card.

Referring now to FIG. 9, another embodiment of an optical system viewing a detection site on a deposable microfluidic array card is illustrated. FIG. 9 is a schematic 90 for the illumination of sites 12 on a disposable microfluidic array card 2 such as that illustrated in FIG. 1. A light source 92 that can be a laser, LED, or bulb generates a beam 94 that is directed to one of sites 12 on card 2. The illuminated site 12 can then be viewed at the eyepiece 58. The light path 54 and mirror 56 are from previous figures.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A microfluidic array card and reader apparatus for analyzing a sample, comprising:
   a microfluidic array card, said microfluidic array card having
   a sample loading section for loading the sample onto said microfluidic array card,
   a multiplicity of array windows, and
   a transport section or sections for transporting the sample from said sample loading section to said array windows; and
   a microfluidic array card reading having
   a housing;
   a receiving section for receiving said microfluidic array card,
   a viewing section, which includes lenses, mirrors, and eyepieces enabling viewing by the individual, and
   a light source that directs light to said array windows of said microfluidic array card and to said viewing section by way of said lenses and mirrors.

2. The microfluidic array card and reader apparatus of claim 1 wherein said array windows include synthetic nucleic acids conjugated to said microfluidic array card.

3. The microfluidic array card and reader apparatus of claim 1 wherein said array windows include synthetic nucleic acids conjugated to beads.

4. The microfluidic array card and reader apparatus of claim 1 wherein said array windows include antibodies conjugated to said microfluidic array card.

5. The microfluidic array card and reader apparatus of claim 1 wherein said array windows include antibodies conjugated to beads.

6. The microfluidic array card and reader apparatus of claim 1 wherein said microfluidic array card further includes an absorbent material adjacent said array windows for causing the sample to wick.

7. The microfluidic array card and reader apparatus of claim 1 wherein said microfluidic array card includes a first layer and a second layer and wherein said first contains said multiplicity of array windows and said transport section or sections.

8. The microfluidic array card and reader apparatus of claim 1 wherein said microfluidic array card reader housing includes hand gripping sections.

9. The microfluidic array card and reader apparatus of claim 1 wherein said microfluidic array card reader includes a light source.

10. The microfluidic array card and reader apparatus of claim 1 wherein said microfluidic array card reader includes a light bulb light source.

11. The microfluidic array card and reader apparatus of claim 1 wherein said microfluidic array card reader includes a laser light, light source.

12. A microfluidic array card and reader apparatus for analyzing a sample, comprising:
   a microfluidic array card, said microfluidic array card having
   a sample loading section for loading the sample onto said microfluidic array card,
   a multiplicity of array windows, and
   a transport section or sections for transporting the sample from said sample loading section to said array windows; and a microfluidic array card reading having
- a housing with hand gripping sections for gripping by the individual;
- a receiving section for receiving said microfluidic array card,
- a viewing section, which includes lenses, mirrors, and eyepieces enabling viewing by the individual, and
- a light source that directs light to said array windows of said microfluidic array card and to said viewing section by way of said lenses and mirrors.

13. The microfluidic array card and reader apparatus of claim 12 wherein said microfluidic array card further includes an absorbent material adjacent said array windows for causing the sample to wick.

14. The microfluidic array card and reader apparatus of claim 12 wherein said microfluidic array card includes a first layer and a second layer and wherein said first contains said multiplicity of array windows and said transport section or sections.

15. The microfluidic array card and reader apparatus of claim 12 wherein said array windows include synthetic nucleic acids conjugated to said microfluidic array card.

16. The microfluidic array card and reader apparatus of claim 12 wherein said array windows include synthetic nucleic acids conjugated to beads.

17. The microfluidic array card and reader apparatus of claim 12 wherein said array windows include antibodies conjugated to said microfluidic array card.

18. The microfluidic array card and reader apparatus of claim 12 wherein said array windows include antibodies conjugated to beads.

19. A microfluidic array card and reader apparatus for analyzing a sample, comprising:
- a microfluidic array card, said microfluidic array card having
  - a sample loading section for loading the sample onto said microfluidic array card,
  - a multiplicity of array windows, and
  - a transport section or sections for transporting the sample from said sample loading section to said array windows; and
- a microfluidic array card reading having
  - a housing with hand gripping sections for gripping by the individual;
  - a receiving section for receiving said microfluidic array card,
  - a viewing section, which includes lenses, mirrors, and eyepieces enabling viewing by the individual, and
  - a light source that directs light to said array windows of said microfluidic array card and to said viewing section by way of said lenses and mirrors, wherein said light source is a light bulb light source or a laser light, light source.

* * * * *